United States Patent [19]

Ekbladh

[11] 4,230,102
[45] Oct. 28, 1980

[54] DEVICE FOR THE TRAINING OF A URINE BLADDER

[75] Inventor: Fred V. G. Ekbladh, Kungsbacka, Sweden

[73] Assignee: Astra-Sjuco AB, Goteborg, Sweden

[21] Appl. No.: 896,746

[22] Filed: Apr. 17, 1978

[30] Foreign Application Priority Data

Apr. 25, 1977 [SE] Sweden ............................. 7704703

[51] Int. Cl.³ ..................... A61F 5/00; A61M 25/00
[52] U.S. Cl. ................................... 128/79; 128/349 R
[58] Field of Search .................... 128/24 R, 64, 60, 68,
128/79, 349 R, 349 B, 349 BV, DIG. 25, 350 R,
350 V, DIG. 24

[56] References Cited

U.S. PATENT DOCUMENTS

| 2,522,108 | 9/1950 | Flagg | 128/350 R |
| 3,503,401 | 3/1970 | Andersen et al. | 128/349 R |
| 3,817,237 | 6/1974 | Bolduc | 128/DIG. 25 |
| 4,053,952 | 10/1977 | Goldstein | 128/DIG. 25 |
| 4,084,593 | 4/1978 | Jarund | 128/DIG. 25 |

FOREIGN PATENT DOCUMENTS

| 837009 | 4/1952 | Fed. Rep. of Germany | 128/349 R |
| 526357 | 9/1976 | U.S.S.R. | 128/DIG. 25 |

Primary Examiner—Lawrence W. Trapp
Attorney, Agent, or Firm—Brumbaugh, Graves, Donohue & Raymond

[57] ABSTRACT

A device for training a urine bladder which has lost its elasticity due to long term catheterization, whereby it comprises a pressure sensitivity system being arranged to the urethra catheter and a closing-opening unit being controlled by said pressure sensitivity system, which unit is arranged after the pressure sensitivity system seen from the urine bladder. A pressure, which is obtained in the catheter, actuates via the pressure sensitivity system a motor which is arranged to open and close the catheter by means of a mechanical clamping unit.

12 Claims, 1 Drawing Figure

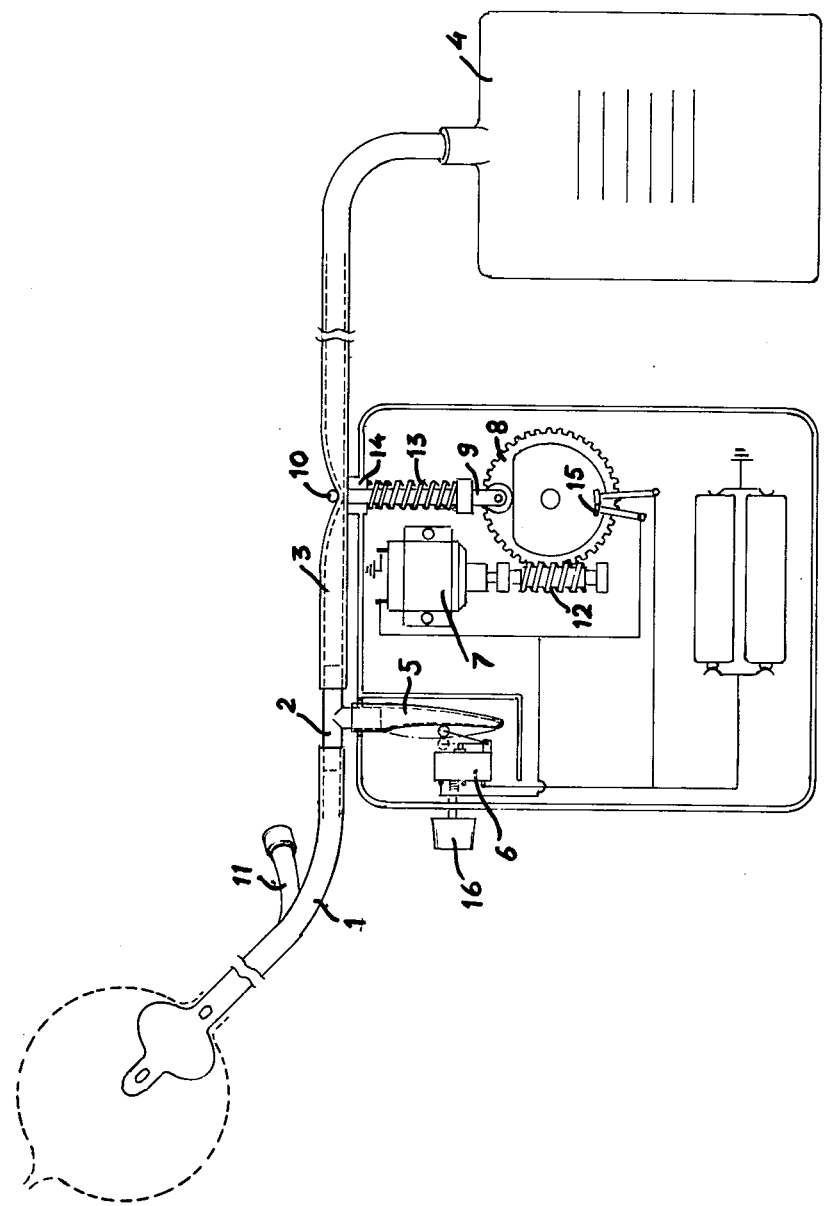

DEVICE FOR THE TRAINING OF A URINE BLADDER

The present invention relates to a device for the training of a urine bladder being catheterized or in any other way elasticity enervated.

The object of the present invention is to obtain a possibility of exercising a urine bladder, which e.g. by way of long term catheterization has been enervated, so that the urine bladder can be filled up to normal volume without influencing the urination reflex to any greater extent.

Long term catheterization of the urine bladder takes place in connection with several surgical incisions of different genesis. At such catheterization a catheter is introduced through the urethra and into the urine bladder and is connected to a so called urine bag, whereupon the urine running into the urine bladder immediately passes on to the urine bag. The sphincter muscle, which normally closes the urine bladder, will after some time become completely enervated and lose its elasticity by way of lack of exercise. Before the removal of the catheter it is thus important that the urine bladder is exercised so that the patient can return to a normal way of living. If urine bladder exercise should not take place, the urine bladder can not be filled as previous but a minimal amount of urine will provoke the urination reflex.

Previously it has been proposed different systems for the exercise of the urine bladder. Thus different systems have been described in U.S. Pat. No. 3,503,401 and Swedish Patent Specification No. 7504312-5 using the siphon effect, where the urine bladder has to work against a column of liquid. The problem of these devices is that they are relatively space requiring and prevent access and care of the patient. This problem has now been eliminated by means of the present invention which is characterized in that the catheter connected to the urine bladder is arranged to a pressure sensitivity system, which controls the opening and the closing of the catheter by means of a closing-opening unit arranged to the catheter, which unit is arranged after the pressure sensitivity system seen from the urine bladder.

According to a preferred embodiment of the invention the pressure sensitivity system is arranged to be controlably varied with regard to the pressure which controls the closing-opening unit, preferably within the pressure range 0–750 mm column of water, (0–0.01 MPa).

According to another preferred embodiment of the invention the pressure sensitivity system controls a revolution controlled motor provided with means for actuating the closing-opening unit, whereby the motor preferably is arranged to open for a time of 1–5 min.

According to a further preferred embodiment of the invention the pressure sensitivity system controls a time relay arranged to control the closing-opening unit, whereby the time relay preferably is arranged to open for a time of 1–5 min.

According to further another preferred embodiment of the invention the motor is arranged to actuate mechanically a closing-opening unit arranged to a flexible tube, said unit being in the form of a unit clamping the tube.

According to another further preferred embodiment of the invention the time relay controls an electromagnetically actuated membrane valve.

The present invention will be described more in detail below with reference to the accompanying drawing, which shows a preferred embodiment.

1 denotes a urethra catheter, which is connected to a T-tube 2. The T-tube 2 is further connected via a flexible tube 3 to a urine bag 4. The third outlet of the T-tube is connected to a pressure membrane 5, which in its turn is arranged to actuate an electric switch 6, when a certain pressure on the T-tube side of the membrane has been obtained. The electric switch is in its turn arranged to give a start impulse to an electric motor 7. An eccentric wheel 8 is mounted via an angle gear 12 to the outgoing shaft of the electric motor 7, which wheel is arranged to actuate a bar 9, which is loaded by means of a spring 13. The bar 9 is further provided with a pressure bar 10 or a pressure plate arranged angularly against the bar 9, whereby the bar 9 is mounted in a holder-on 14 cooperating with the pressure bar 10. The tube 3 is hereby arranged between the pressure bar 10 and the holder-on 14. On the eccentric wheel 8 an electric switch 15 is further arranged so that when the wheel 8 has revolved one revolution the electric current to the motor 7 is switched off. The motor 7 is thus arranged to revolve the eccentric wheel 8 one revolution only, when a provoking pressure has been obtained. The speed of the motor 7 and/or the gear ratio of the angle gear can hereby be varied so that a revolving of one revolution of the eccentric wheel 8 takes 1–5 min.

The pressure membrane 5 is further adjustably arranged via an adjusting screw 16 so that the pressure which provokes the switch 6 can be varied between 0–750 mm column of water (0–0.01 MPa).

Further, the catheter 1 can be provided with a further T-tube 11, through which flushing liquid for the flushing and cleaning of the urine bladder can be carried out.

The device according to the invention functions as follows: When urine is excreted through the urine bladder and the urethra catheter a pressure will be built up in the catheter as the tube 3 is closed by means of the pressure bar 10. When the pressure in the catheter has reached the predetermined pressure, which is determined by the condition of and the normal bladder pressure of the patient and which has been adjusted to on the pressure membrane 5, the pressure membrane 5 will actuate the switch 6, which closes the electric current to the electric motor 7. The motor shaft of the motor is hereby revolved one revolution for a time of e.g. 2 min., whereby the eccentric wheel mounted on the shaft actuates the bar 9, which thereby raises the pressure bar 10 so that the tube 3 is opened and the urine can flow down into the urine bag 4. When the eccentric wheel has completed one revolution the tube 3 is closed again via the pressure bar 10 and a new pressure and a new dilatation of the urine bladder can take place.

As the provoking pressure of the pressure membrane can be varied and the revolution time of the motor can be varied the exercise of the bladder can be changed with regard to the condition of the patient. Thus in the beginning of the bladder exercise period a lower provoking pressure and a longer revolution time is used while when the patient's urine bladder has been more exercised a greater pressure and a shorter revolution time is used.

The catheter is preferably a so called baloon catheter, i.e. that the end introduced into the urine bladder is provided with a separately inflatable baloon intended to retain the catheter in the urine bladder.

Within the scope of the invention other pressure sensitivity system than pressure membranes can be used as well for the registration of pressure and the control of the opening of the catheter.

Likewise within the scope of the invention the motor having arranged thereto mechanical units for closing and opening of the catheter can be exchanged with another device. Thus an electromagnetically actuated valve can be arranged in the catheter whereby the valve is suitably a membrane valve in order to reduce the risk of bacterial contamination and/or corrosion of metal valves. A compressed air source can be used as well for the closing and opening of the catheter.

It is evident that any sudden pressure increase in the catheter e.g. caused by coughing or other pressure on the abdomen, will cause the pressure sensitivity system to actuate the opening of the catheter. It is thus also evident that a time relay should be arranged to the opening-closing unit, which relay delays the opening of the catheter up to about one minute, whereby attacks of coughing or external pressure on the abdomen, e.g. leaning against a table edge, are eliminated. The time relay may be replaced by a mechanical means which equalizes a sudden increase of pressure in the catheter. Thus the third outlet of the T-tube 2 may be connected to a hollow space filled with pressure absorbing material or to a membrane having a reducing valve, as e.g. a jet valve, in order to create a pressure equalizing system.

I claim:

1. A device for exercising a urine bladder into which a catheter has been inserted, comprising closing-opening means engaging said catheter, said closing-opening means being normally closed for preventing flow through said catheter, means for detecting the pressure in said catheter between said bladder and said closing-opening means, and actuation means coupled to the pressure detecting means for opening said closing-opening means for a pre-set time period to permit flow through said catheter in response to the detection of a predetermined pressure by said pressure detecting means, said pre-set time period being sufficient to permit said bladder to empty at least substantially, wherein said actuation means is adjustable for opening said closing-opening means at one of a plurality of predetermined pressures in said catheter.

2. A device according to claim 1, wherein said actuation means comprises a revolution controlled motor and coupling means between said motor and said closing-opening means.

3. A device according to claim 2, wherein said closing-opening means comprises clamping means engaging said catheter and said coupling means is arranged to release said clamping means when said motor is actuated.

4. A device according to claim 1, wherein said actuation means comprises a time relay means for controlling said closing-opening means.

5. A device according to claim 4, wherein said closing-opening means comprises an electromechanically controlled membrane valve and wherein said time relay is arranged to control said valve.

6. A device according to claim 1, further comprising means communicating with said catheter for introducing a liquid into said urine bladder.

7. A device according to claim 1, wherein said actuation means is adjustable for opening said closing-opening means in response to a detected pressure between 0 and 750 mm. column of water in said catheter.

8. A device according to claim 2, wherein said motor and said coupling means are adapted to open said closing-opening means for a time period of 1-5 minutes upon actuation of said motor by said actuation means.

9. A device according to claim 4, wherein said time relay is adapted to open said closing-opening means for a time period of 1-5 minutes.

10. A device according to claim 1, comprising means for preventing opening of said closing-opening means in response to momentary surges of pressure in said catheter.

11. A device according to claim 10, wherein said means for preventing opening of said closing-opening means in response to momentary surges comprises a time delay means acting on said actuation means.

12. A device according to claim 1, comprising pressure equalizing means coupled to said catheter between said pressure detecting means and said bladder for preventing opening of said closing-opening means in response to momentary surges of pressure in said catheter.

* * * * *